Figure 1:
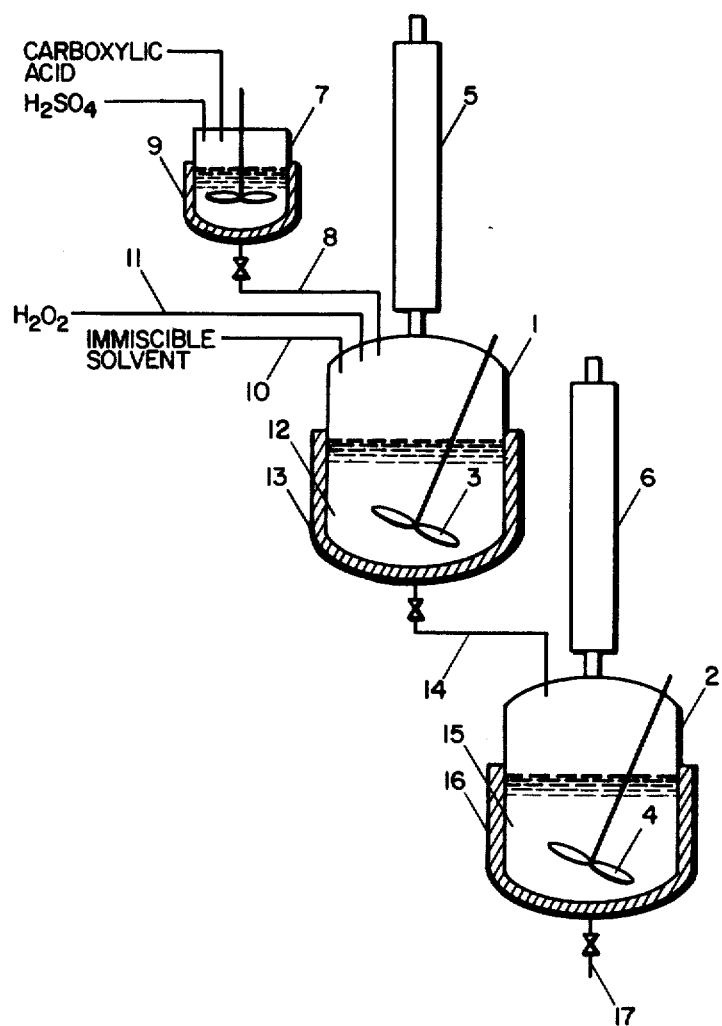

United States Patent [19]

Liao et al.

[11] 4,370,251
[45] Jan. 25, 1983

[54] CONTINUOUS PROCESS FOR THE PRODUCTION OF PEROXYCARBOXYLIC ACID COMPOSITIONS

[75] Inventors: Hsiang P. Liao, Princeton; Richard A. Mohr, Martinsville; John F. Start, Trenton, all of N.J.

[73] Assignee: FMC Corporation, Philadelphia, Pa.

[21] Appl. No.: 172,329

[22] Filed: Jul. 25, 1980

[51] Int. Cl.$^3$ .................. C01B 15/10; C07C 179/10
[52] U.S. Cl. .................. 252/186.42; 252/186.26; 260/502 R
[58] Field of Search .............. 252/186, 186.42, 186.26; 260/502 R

[56] References Cited

U.S. PATENT DOCUMENTS

| 3,092,587 | 6/1963 | Ester et al. | 252/186 |
| 3,140,312 | 7/1964 | Kurhajec et al. | 252/186 |
| 3,169,986 | 2/1965 | Webb et al. | 252/186 |
| 4,071,541 | 1/1978 | Hildon et al. | 252/186 |
| 4,087,455 | 5/1978 | Prescher et al. | 252/186 |
| 4,172,086 | 10/1979 | Berkowitz | 252/186 |

FOREIGN PATENT DOCUMENTS

| 970 | 6/1978 | European Pat. Off. | 252/186 |
| 4039390 | 3/1977 | Japan | 252/186 |
| 1330877 | 12/1970 | United Kingdom | 252/186 |

OTHER PUBLICATIONS

Merck Index, 7th Ed., Merck & Co., Inc., Rahway, NJ 1960, p. 947.

*Primary Examiner*—Henry R. Jiles
*Assistant Examiner*—Robert C. Whittenbaugh
*Attorney, Agent, or Firm*—Edwin B. Cave; Frank Ianno

[57] ABSTRACT

Peroxycarboxylic acid compositions containing stabilizing ingredients are produced by the hydrogen peroxide peroxidation of corresponding carboxylic acids which are not substantially soluble in water by a continuous process in which the peroxidation reaction takes place in solution in concentrated sulfuric acid, or other strong acid, while that solution is intimately interdispersed, by means of agitation, with methylene chloride, or other organic solvent, in which the resulting peroxycarboxylic acid is soluble, but the carboxylic acid is not, and the sulfuric acid, or other acid, is recovered from the effluent of the process by reacting it with borax and caustic soda or soda ash to form crystals of boric acid and sodium salt of the strong acid which, in admixture with peroxycarboxylic acid recovered from the effluent, form the peroxycarboxylic acid composition product. The methylene chloride is also recovered from the effluent and recycled to the process.

9 Claims, 3 Drawing Figures

CONTINUOUS PROCESS FOR THE PRODUCTION OF PEROXYCARBOXYLIC ACID COMPOSITIONS

This invention relates to processes for the production of peroxycarboxylic acid compositions from the corresponding carboxylic acids and is particularly concerned with the carrying out of such processes in a continuous manner.

Peroxycarboxylic acids are used as bleaching agents in dry bleach mixtures or detergent mixtures which often contain, among other ingredients, boric acid and sodium sulfate as stabilizers to minimize decomposition of the peroxyacid. Such mixtures can conveniently be produced by the continuous process of the present invention.

Techniques for producing peroxycarboxylic acids by subjecting carboxylic acids to the action of hydrogen peroxide in a common solution have been extensively developed in the prior art. The applicability of particular of these techniques to particular carboxylic acids has depended, among other things, upon the chain length of, or number of carbon atoms in, the acid molecule, and whether it is monocarboxylic or polycarboxylic, aliphatic or aromatic, saturated or unsaturated. Among the limiting factors are the solubilities of the carboxylic acid and its peroxy derivative in various aqueous and organic solvent solutions and the stability of the product under various conditions.

With carboxylic acids having no substantial solubility in water, the mutual solubility required for interaction with hydrogen peroxide has been achieved in the art by using a strong acid, usually concentrated sulfuric acid or oleum, as a solvent for the carboxylic acid.

In European Patent Application No. 970, it is proposed that the peroxidation of certain of such water-insoluble carboxylic acids, namely long chain alkylene dicarboxylic acids, be carried out by a continuous process in which the dicarboxylic acid dissolved in concentrated sulfuric acid is continuously introduced along with hydrogen peroxide and water into a stirred tank reactor, in which it is subjected to low shear mixing, as by a slowly moving paddle agitator, and a portion of the reaction mass is continuously removed from the reactor. The peroxycarboxylic acids so produced are mixed with various additives including boric acid and various salts.

A particularly effective procedure for carrying out the peroxidation of carboxylic acids other than the water soluble lower aliphatic acids, particularly when such acids are dicarboxylic, is that described in U.S. Pat. No. 4,172,086.

In the process of that patent, the reaction of concentrated aqueous hydrogen peroxide with a carboxylic acid dissolved in concentrated sulfuric or organo-sulfonic acid as a solvent-catalyst is effected more rapidly and completely in a safer, more easily controlled operation by intimately dispersing throughout the reaction mixture, by vigorous agitation, an inert, water-immiscible solvent for the resulting peroxycarboxylic acid.

By removing the peroxy product from the aqueous medium in which the reaction is taking place, the presence of the water-immiscible solvent shifts the equilibrium toward conversion of the carboxylic acid to the peroxy product and also reduces the deteriorating effect of the acid upon the product. Moreover, when the water-immiscible solvent has a boiling point substantially below temperatures at which the exothermic peroxidation reaction becomes dangerously accelerated, the boiling of the solvent in intimate dispersion throughout the aqueous reaction mixture reduces the hazard of development of explosive conditions. When the boiling point of the solvent under the operating pressure is at the desired temperature of reaction, the reaction can be carried out under reflux with precise built-in control of the reaction temperature.

At the conclusion of the reaction, the peroxyacid product of that procedure is described as recoverable in several ways. The reaction mass can be allowed to separate into the water-immiscible solvent phase and the aqueous phase. After decantation of the solvent phase, the peroxyacid product can be recovered therefrom by cooling to cause product crystallization or by removal of the solvent by distillation. Alternatively, the reaction mass can be diluted by a substantial amount of water, after which the solvent can be removed by distillation and the solid product separated from the remaining aqueous liquid. In this process the strongly acid aqueous liquid remaining after recovery of the peroxycarboxylic acid can present a disposal problem. The acid, diluted by the reaction and subsequent processing, cannot be recovered for reuse in the process without an expensive concentration procedure and cannot be discarded without prior neutralization.

The continuous process of the present invention comprises a peroxidation which is particularly applicable, but not limited, to the longer chain saturated aliphatic acids, and particularly the dicarboxylic acids, and which is carried out in a vessel, or in a plurality of serially connected vessels, each being so dimensioned and so equipped as to provide sufficiently vigorous agitation, as by vigorous stirring, to create and maintain an intimate interdispersion of the immiscible contents so as to prevent collection at any point of a significant body of an unstable phase of reactants.

There is first established in the single vessel or in each of the series of successively connected vessels an essentially integral liquid reaction mass comprising carboxylic acids, concentrated hydrogen peroxide, concentrated strong acid in which the carboxylic acid is substantially soluble and resulting reaction products, said reaction mass also comprising, intimately dispersed therethrough, a water-immiscible organic solvent in which the peroxy derivative of the carboxylic acid is substantially more soluble than is the carboxylic acid.

Thereafter, while said mass is maintained at a temperature at which the carboxylic acid is peroxidized by the hydrogen peroxide and while the mass is continuously agitated sufficiently to maintain said interdispersion, there is continuously introduced into said single vessel, or into the first of said series of vessels, an amount of said carboxylic acid dissolved in concentrated sulfuric acid or other strong acid as solvent-catalyst, an amount of said organic solvent recycled from a later stage of the process, and an amount of concentrated hydrogen peroxide separate from said sulfuric acid solution of carboxylic acid, and there is continuously withdrawn from said vessel a portion of said mass in equivalent amount so as to maintain an essentially fixed total quantity of material in said vessel. When a series of vessels is employed, the withdrawn portion is continuously introduced into the next succeeding vessel and a like amount is continuously withdrawn from each succeeding vessel and passed into the next.

The continuous introduction of reactants into the system and withdrawal of a portion of the reaction mass from the system is carried out at a rate such that the total residence time in the system is sufficient to result in the desired degree of conversion of carboxylic acid to peroxycarboxylic acid. Sufficient organic solvent is introduced into and maintained in the system, in comparison to the rest of the reaction mass, to take into solution the bulk of the peroxycarboxylic acid produced so that very little or substantially none accumulates in the aqueous phase. The proportion of organic solvent is also sufficient to dilute thermally the exothermic reaction and thus prevent excessive local or overall temperature rise. The reaction vessels are equipped with reflux condensers to return solvent vapors generated during the reaction.

The effluent of the system comprises essentially a mixture of an aqueous phase made up primarily of sulfuric acid, or other strong acid, of somewhat lower concentration than that introduced into the reactor system and an organic solvent phase containing dissolved peroxycarboxylic acid. Components of this mixture are recovered by a continuous procedure in which the acid of the aqueous phase is neutralized with borax and as much of a source of soda, which can be caustic soda or soda ash, as required for pH control, resulting in formation of a slurry of crystals of boric acid and sodium salt of the acid, which crystals are combined with peroxycarboxylic acid recovered from the organic solvent phase to produce a mixed product, to which other additives can be added if desired to produce the final stabilized peroxyacid product. The separation of the peroxycarboxylic acid from the organic solvent is accomplished by distilling off the solvent or by cooling the solvent phase to crystallize out the peroxyacid. The organic solvent is recycled to the reactor system.

This treatment of the withdrawn portion to produce the final mixed peroxyacid composition can be carried out in several ways. In a preferred embodiment, the withdrawn mixture is first diluted by continuously recycling neutralized aqueous phase derived from previous withdrawn portions of the reaction mass. This aqueous diluent can contain crystals of boric acid and sodium salt resulting from neutralization of the sulfuric or other acid with borax and caustic soda, or soda ash, or this diluent can be the solid-free residual aqueous liquor after these crystals have been separated by filtration or centrifuging. The organic solvent is then evaporated from the mixture and recycled, leaving an aqueous liquid mixed with crystals of either peroxyacid alone or of peroxyacid together with boric acid and sodium sulfate or other sodium salt, depending upon the composition of the aqueous diluent.

If the resulting solid component is peroxyacid alone, borax and any necessary caustic soda or soda ash are added to the residue after solvent evaporation to neutralize residual acid, resulting in a solid component containing peroxyacid, boric acid and sodium sulfate or other sodium salt which is separated from the aqueous liquid by filtration or centrifuging and becomes, after blending if desired with other additives, the stabilized peroxycarboxylic acid product.

If, on the other hand, the solid component after dilution and solvent evaporation is made up of peroxyacid together with boric acid and sodium sulfate or other sodium salt, this solid component is separated by filtration or centrifuging and washed and becomes, after blending if desired with other additives, the stabilized peroxycarboxylic acid product. The residual aqueous liquid, still containing the acid from the reaction mass, is neutralized with borax and any necessary caustic soda or soda ash, resulting in an aqueous slurry of boric acid and sodium sulfate or other sodium salt which is recycled to the dilution step of the process.

Alternatively, the portion withdrawn from the reactor system can be continuously passed to a decanter in which the organic solvent phase is separated from the aqueous phase. Peroxyacid is recovered from the separated organic solvent phase by evaporation of the solvent or by cooling the solvent to crystallize the peroxyacid. Solvent is recycled to the reactor system. Borax and any necessary caustic soda, or soda ash, are added to the separated aqueous phase to neutralize the acid and produce crystals of boric acid and sodium sulfate or other sodium salt, which after separation from the aqueous liquor are blended with the peracid to form the stabilized product, with or without other additives.

Figure 2:
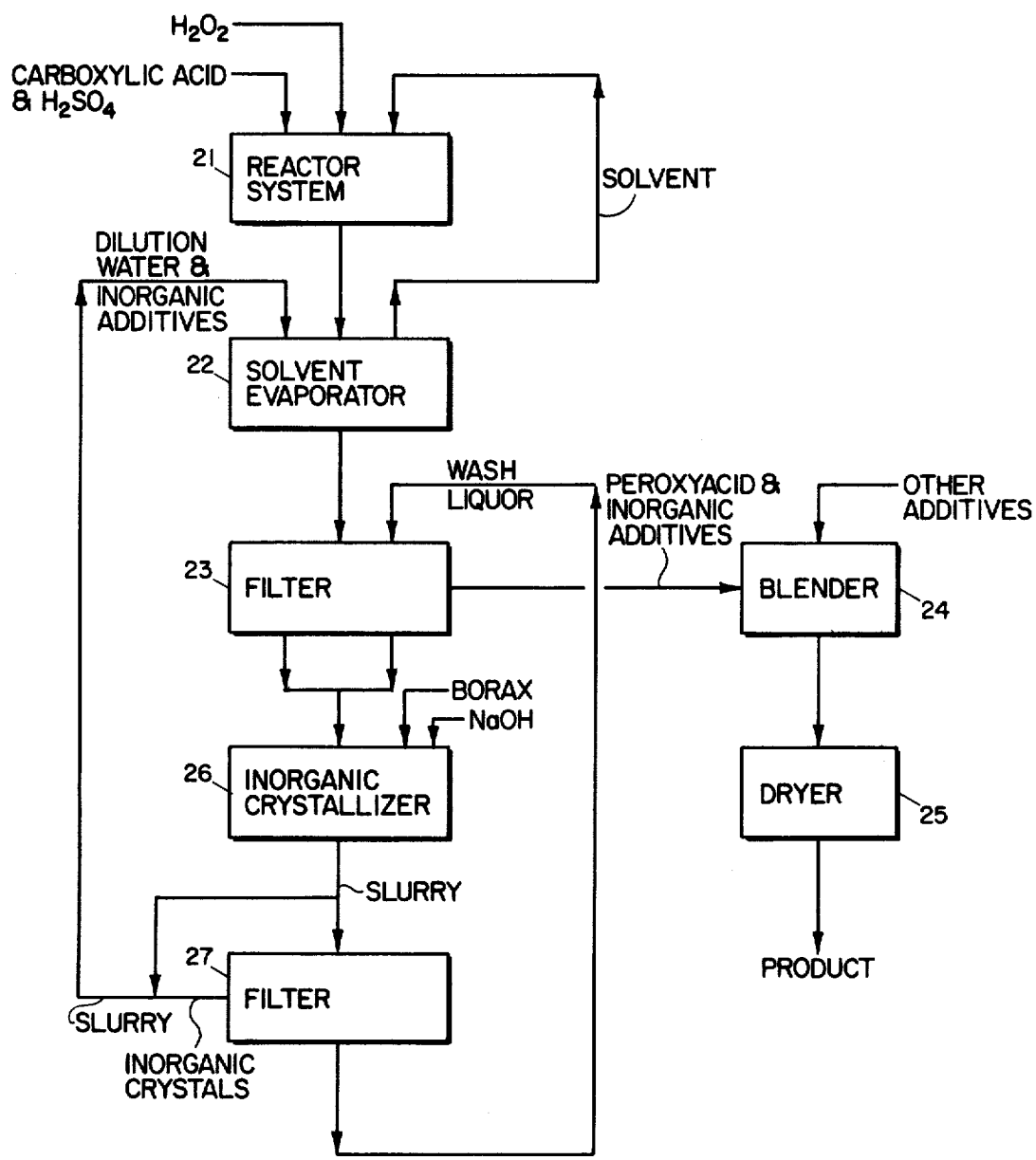
Figure 3:
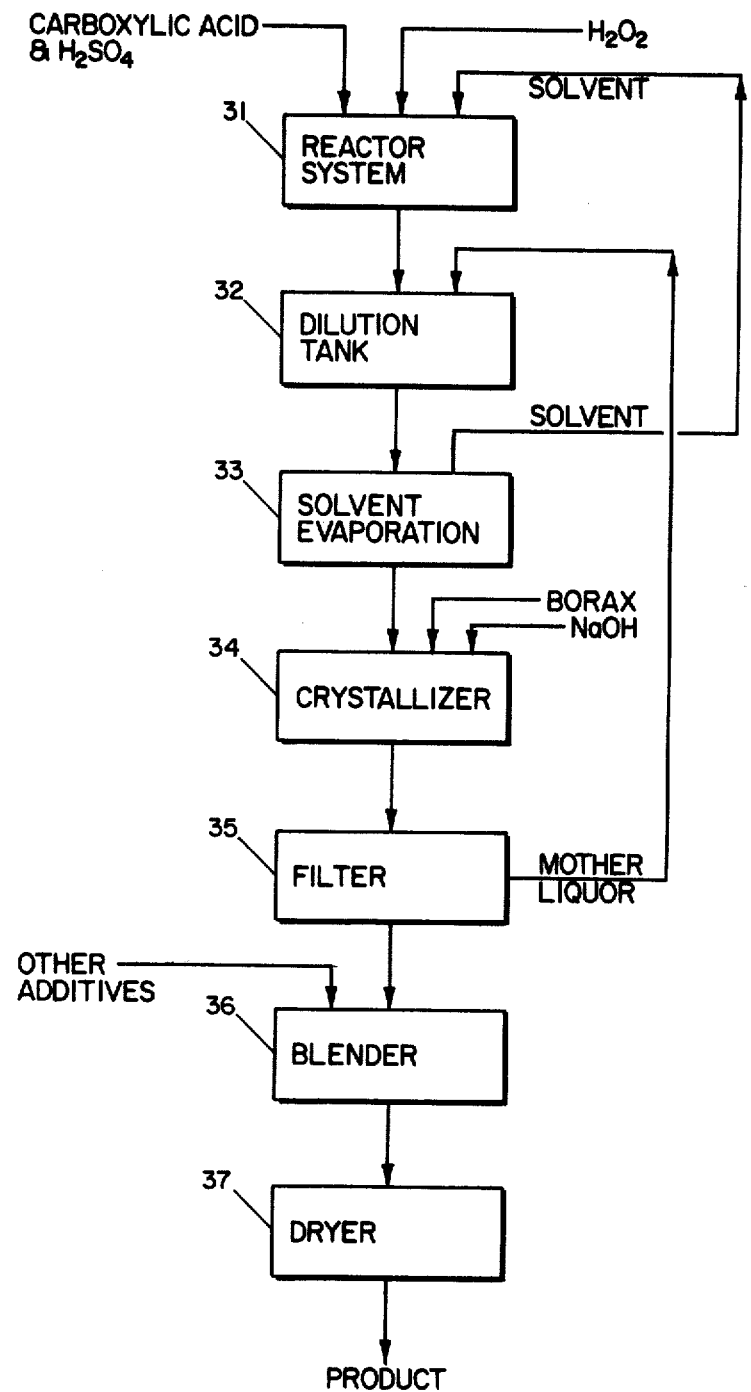

In the accompanying drawing,

FIG. 1 is a diagrammatic representation of one embodiment of one form of reactor system in which the continuous peroxidation of carboxylic acid with hydrogen peroxide to produce peroxycarboxylic acid can be carried out in accordance with the present invention;

FIG. 2 is a flow chart representing diagrammatically one procedure in accordance with the present invention for continuously producing peroxycarboxylic acid compositions containing stabilizing additives; and FIG. 3 is a flow chart representing an alternative procedure for continuously producing peroxycarboxylic acid compositions containing stabilizing additives in accordance with the present invention.

In the preferred embodiment shown in FIG. 1, the reaction is carried out in two serially connected stationary vessels 1, 2. These enclosed vessels are equipped with stirring devices 3, 4 and are vented through reflux condensers 5, 6. A separate vessel 7 is also provided in which the carboxylic acid is maintained in solution in concentrated sulfuric acid or other strong acid solvent catalyst, and from which this solution is continuously supplied in controlled amount through duct 8 to vessel 1. If the proportions of carboxylic acid and concentrated sulfuric acid, or other strong acid solvent-catalyst, in vessel 7 are such that the carboxylic acid would not be fully soluble if vessel 7 were maintained at temperatures up to the reaction temperature in vessel 1, it is desirable, where possible, to maintain the temperature of vessel 7 by means of heating jacket 9 at such higher temperature as will maintain complete solubility so that the amount and proportions of carboxylic acid and solvent-catalyst introduced into vessel 1 can be accurately controlled.

Concentrated hydrogen peroxide and immiscible organic solvent recycled from the process as shown, for instance, in FIGS. 2 and 3, are continuously introduced in controlled amounts by means of ducts 11 and 10. The reaction mass 12 in vessel 1 then consists of an aqueous reaction phase and an organic solvent phase maintained continuously in intimate interdispersion by means of stirrer 3. Heat from the exothermic peroxidation reaction is continuously carried away by the vaporization of organic solvent, the vapors being condensed in condenser 5 and returned to the vessel. Make up heat where necessary to maintain the reaction temperature is supplied by heating jacket 13.

A portion of the interdispersion making up the reaction mass 12 in vessel 1 is continuously transferred in controlled amount by means of duct 14 to vessel 2 where it is added to the reaction mass 15 already present. The interdispersion of the immiscible components of mass 15 is continuously maintained by means of stirrer 4 and heat is continuously removed by vaporization of organic solvent, the evolved vapors being condensed in condenser 6 and returned to the vessel. Any make up heat required to maintain the reaction temperature is supplied by heating jacket 16.

A portion of the interdispersion making up the reaction mass 15 in vessel 2 is continuously withdrawn by means of duct 17.

The rates of introduction of material through ducts 8, 10, 11, the transfer of material through duct 14 and the withdrawal through duct 17 are controlled so that the amount of material in each of masses 12 and 15 remains substantially constant and so that the effective combined total residence time of the reaction mixture in the two vessels is sufficient to permit the required degree of completion of the peroxidation reaction.

The manner in which this continuous production of peroxycarboxylic acids is incorporated into the overall process of the present invention for production of peroxycarboxylic acid compositions containing stabilizing ingredients is illustrated in the embodiments shown in the flow charts of FIGS. 2 and 3.

In the procedure of FIG. 2, the effluent from reactor system 21, which can be the embodiment shown in FIG. 1, is mixed with an aqueous diluent slurry recycled from the process and containing boric acid and sodium sulfate crystals derived by neutralization of the acid in the aqueous phase of priorly treated effluent and the mixture is introduced into solvent evaporator 22 in which the solvent is distilled from the solvent phase of the effluent and is recycled to the reactor system. The depletion of the solvent from the solvent phase leaves the previously dissolved peroxyacid in solid crystalline form in the aqueous phase together with the previously introduced boric acid and sodium salt crystals. The resulting solid and liquid mixture is passed to filter 23, where the solid crystals are separated and after washing in recycled neutralized mother liquor are blended, if desired, with other additives in blender 24, dried in dryer 25 and recovered as stabilized peroxycarboxylic acid product. The filtrate from filter 23 together with the wash liquor are passed to crystallizer 26 to which borax and caustic soda or soda ash, are added to neutralize the acid and produce an aqueous slurry of boric acid and sodium sulfate crystals. A portion of this slurry is filtered in filter 27 to produce a neutral filtrate which is used to wash the crystals separated in filter 23. The solids separated in filter 27 are reintroduced into the remaining portion of the slurry from crystallizer 26 and this slurry is then returned to the dilution of the effluent of the reactor system.

In the embodiment shown in FIG. 3, the effluent from reactor system 31, which can be the embodiment shown in FIG. 1, is diluted in dilution tank 32 with recycled solid-free neutralized mother liquor produced from priorly treated reactor effluent. The solvent is distilled from the diluted effluent in solvent evaporator 33 and is recycled to the reactor system. The aqueous liquid remaining after solvent removal, together with the peroxyacid crystals discharged from solution are passed to crystallizer 34 where borax and caustic soda, or soda ash, are added to neutralize the sulfuric acid and generate crystals of boric acid and sodium sulfate resulting mixture being passed to filter 35 where the solid and liquid components are separated. The separated mother liquor is recycled to dilution tank 32. The solid component made up of crystals of peroxyacid, boric acid and sodium sulfate can, if desired, have other additives incorporated in blender 36 before being dried in dryer 37 to produce the final stabilized peroxycarboxylic acid composition.

The following Examples 1 and 2 illustrate embodiments of the initial steps of the process of the present invention, namely a continuous procedure for the hydrogen peroxide treatment of carboxylic acid, dissolved in a strong acid, in the presence of an interdispersed immiscible solvent for the resulting peroxyacid. Example 3 sets forth results obtained with the neutralization of an aqueous slurry produced by repetitive batch processing and illustrates one procedure which can also be applied to the processing of residual acidic aqueous slurries of peroxycarboxylic acids produced by continuous peroxidation of carboxylic acids in solution in concentrated sulfuric acid.

EXAMPLE 1

Single Stage Peroxidation

A master batch feed charge of dodecanedioic acid (DDA) dissolved in concentrated sulfuric acid was established by stirring 230 grams (1 mole) of pulverized dodecanedioic acid with 350 grams (3.5 moles) of 98% sulfuric acid at 50° C. until a yellow solution was effected. This solution was placed in a 250 ml heated charge funnel which was maintained at 45° C.-50° C. to prevent crystallization of the dissolved DDA. An initial charge was established in a 4-neck glass spherical reactor, equipped with a rotary stirrer, an external heater and a reflux condenser, by introducing 360 ml of methylene chloride, which was heated to 40° C., introducing 61.74 ml of the feed (containing 0.15 mole of DDA), agitating by stirring at 500 rpm to disperse the two liquid phases and then introducing over a 5 minute interval 18 ml (0.47 mole) of 70% aqueous hydrogen peroxide. After reaction had been allowed to proceed for 15 minutes at 40° C. with continuous stirring at 500 rpm and sufficient heat input to cause a gentle reflux, continuous simultaneous charging and discharging of the reactor was begun. The charge in the reactor was maintained at its initial volume of 440 ml by continuously pumping the reaction mass out of the reactor at a rate of 7.3 ml per minute while continuously introducing the DDA-sulfuric acid feed at 1.029 ml per minute, 70% hydrogen peroxide at 0.3 ml per minute and methylene chloride at 6 ml per minute (molar ratios of $H_2SO_4:H_2O_2:DDA$ equal to 3.5:3.125:1). The effective residence time of the reaction mass in the reactor during continuous operation (volume of reaction mass in reactor divided by pump rate) was 60 minutes. After continuous operation had continued for 4 hours at 40° C. with continuous stirring and gentle reflux, the effectiveness of the reaction was tested by taking samples of effluent at the discharge pump exit in 20 ml portions at the fourth hour and at each half hour thereafter until the end of 5½ hours. Each such 20 ml sample was processed by quenching immediately with ice-cold distilled water, stripping the methylene chloride in a rotating evaporator at 25° C. at an absolute pressure of 15 to 20 torr., washing the resulting aqueous concentrate with distilled water while filtering until the filtrate fell within a pH range of 3 to 3.5, and drying the filter-stripped solids in vacuo (0.2 torr. absolute) at 25° C. for a minimum of 15 hours until constant weight was reached. Without delay the dried white solids were iodometrically analyzed in duplicate for active oxygen content from which data assays of diperoxydodecanedioic acid (DPDA) were calculated. The results were as follows:

| Time Sample was Taken | Duplicate Assay (% DPDA) |
| --- | --- |
| 4 hrs. | 93.37 |
|  | 93.46 |
| 4½ hrs. | 93.63 |
|  | 94.07 |
| 5 hrs. | 91.94 |
|  | 91.69 |
| 5½ hrs. | 92.42 |
|  | 92.84 |
| Arithmetic mean | 92.92 |

The DPDA assay by iodometric analysis was carried out as follows: A sample of ca. 500 mg weighed to the nearest tenth of a milligram was charged to a 250 ml Erlenmeyer flask, and to the flask was added about 30 ml of acetone, in which the sample quickly dissolved, followed by 20% aqueous sulfuric acid, about 200 mg of potassium iodide and several drops of saturated aqueous ammonium molybdate. The resulting solution was immediately titrated with 0.1 N aqueous thiosulfate to a colorless endpoint. The percentage of DPDA was calculated as 6.55×ml thiosulfate solution×normality divided by the weight of the sample in grams.

EXAMPLE 2

Two Stage Peroxidation

The flows and concentrations were as described in Example 1. A secondary reactor similar to the primary was inserted in the system such that effluent from the primary was pumped to the secondary. When the 220 ml level was attained in the primary, the reaction mass was discharged to the secondary instead of a product receiver. When the 220 ml level was attained in the heated (40° C.) and agitated (500 rpm) secondary, the reaction mass was pumped continuously to the product receiver. Effective residence time in each reactor was 30 minutes, making a total residence time of 60 minutes for the system. In-process sampling and DPDA assays were carried out as in Example 1 and are as follows:

| Time at which Sample was Taken | Duplicate Assays (% DPDA) |
| --- | --- |
| 4 hours | 96.43 |
|  | 96.53 |
| 4½ hrs. | 96.21 |
|  | 96.42 |
| 5 hrs. | 93.55 |
|  | 95.04 |
| 5½ hrs. | 96.31 |
|  | 96.32 |
| Arithmetic mean | 95.8 |

EXAMPLE 3

Neutralization

An aqueous slurry of diperoxydodecanedioic acid resulting from the reaction of 93.3 grams of 35% aqueous hydrogen peroxide with 72 grams of dodecanedioic acid in 344 grams of 97% sulfuric acid was diluted with 1,170 grams of mother liquor (saturated with boric acid and sodium sulfate) from earlier reaction of the same ingredients in the same proportions. This diluted mixture was neutralized by adding 165 grams of borax decahydrate and sufficient sodium hydroxide (469 grams of NaOH added as 50% aqueous solution) to bring the pH to 3.0. The mother liquor used for dilution was obtained by evaporating 247 grams of water from the total available mother liquor of 1,447 grams resulting from the prior step. The temperature during dilution and neutralization was maintained at between 35° C. and 40° C. The resulting slurry was filtered and the filter cake was dried, yielding a product which was found to contain by weight 11.32% diperoxydodecanedioic acid, 72.73% sodium sulfate and 15.23% boric acid.

The procedure of these examples can similarly be advantageously applied to the preparation of peroxycarboxylic acid compositions from other alkane dicarboxylic acids having low solubility in water or alkane monocarboxylic acids of similar low solubility, particularly those mono- or dicarboxylic acids containing more than six carbon atoms and up to about twenty carbon atoms. Moreover, other aliphatic or aromatic hydrocarbon dicarboxylic or monocarboxylic acids of low water solubility or substantial insolubility or substituted aliphatic or aromatic hydrocarbon dicarboxylic or monocarboxylic acids of low water solubility or substantial insolubility, which are substantially soluble in a strong acid solvent-catalyst and which are stable against reaction other than peroxidation in the presence of such a strong acid and concentrated hydrogen peroxide can also be continuously peroxidized in carrying out the present invention, to produce the corresponding mono- or diperoxycarboxylic acid.

The preferred strong acid used as the solvent-catalyst is concentrated sulfuric acid when carboxylic acids are being peroxidized which contain no bonds or groups substantially reactive with the sulfuric acid under the conditions of operation. Thus in the peroxidation of the aliphatic carboxylic acids, sulfuric acid is preferred. The concentration of the sulfuric acid can vary between 10% molar excess of $H_2O$ beyond the stoichiometric ratio of $H_2O$ to $SO_3$ in $H_2SO_4$ and a 20% excess of $SO_3$ (oleum). The preferable range of concentration is from a 4% molar excess of $H_2O$ to a 4% excess of $SO_3$.

Among other suitable strong acid solvent-catalysts for use in the process of the present invention are the organosulfonic acids, examples being methane sulfonic acid, trifluoro methane sulfonic acid and toluene sulfonic acid. Methane sulfonic acid is preferred with aromatic carboxylic acids where the benzene ring tends to be sulfonated by sulfuric acid.

The aqueous hydrogen peroxide used in the process should have a concentration by weight between 30% and 100% and preferably between 40% and 50%.

In place of the methylene chloride referred to above, other organic solvents can be used as the diluent-solvent which are essentially water-immiscible, unreactive toward the concentrated hydrogen peroxide and strong acid catalyst, capable of dissolving the peroxycarboxylic acid as it forms while having only a limited solvent capacity for the parent carboxylic acid at the reaction temperature and capable of dissipating the exothermic heat of reaction to prevent local overheating. Benzene and toluene and other aromatic hydrocarbons, as well as other halogenated aliphatic or aromatic hydrocarbons having boiling points at or above the reaction temperature at the operating pressure but low enough that vaporization will dissipate excessive local heat of reaction, preferably in the range of about 25° C. to about 100° C. at the operating pressure can be used. It is ordinarily desirable that the boiling point of the solvent be at or close to the reaction temperature. It is ordinarily convenient to carry out the reaction at essentially atmospheric pressure but where desired, subatmospheric or superatmospheric pressures can be used.

The amount of diluent solvent present in the reaction mass should be sufficient to dissolve the bulk of or substantially all the peroxycarboxylic acid produced in the process and sufficient to prevent local overheating by dissipating the exothermic heat of reaction. Ordinarily the volume of diluent solvent will be at least about four times, and preferably five times, the volume of the aqueous phase. For economic reasons it is ordinarily not advantageous to use a volume of diluent solvent in excess of seven times that of the aqueous phase although the process will be operative with larger volumes.

The reaction is ordinarily most effectively carried out in the temperature range between about 25° C. and 100° C. the optimum temperature varying from about 25° C. to 35° C. for the carboxylic acids containing the smaller number of carbon atoms to about 35° C. to 50° C. for the high acids.

The molar ratio of strong acid solvent-catalyst to carboxylic acid introduced into the reaction mass will ordinarily lie between 2:1 and 5:1 and is preferably between 3:1 and 3.5:1. The molar ratio of hydrogen peroxide to carboxylic acid will ordinarily lie between 2:1 and 5:1, preferably between 3:1 and 3.5:1, for dicarboxylic acids and between 1:1 and 2.5:1, preferably between 1.5:1 and 1.8:1 for monocarboxylic acids.

The rate of introduction of reactants into and withdrawal from the reaction vessels, in comparison to the amount of material retained within the reaction vessel, will ordinarily be chosen to give an effective residence time of at least 30 minutes but not in excess of 2 hours. One hour residence will ordinarily be found effective, but shorter times down to 30 minutes may be found desirable for the acids containing a smaller number of carbon atoms.

In carrying out the neutralization of sulfuric acid in the effluent by addition of borax and an effective source of caustic soda (either caustic soda or soda ash), the temperature is desirably maintained above the temperatures (25° C.-32° C.) at which sodium sulfate crystallizes in the form of the heptahydrate and decahydrate since such hydration requires additional evaporation in subsequent drying. Moreover, at those lower temperatures unstable supersaturation tends to occur, resulting in inconsistent yields of solid product. Temperatures sufficiently high to result in excessive decomposition of peroxyacid should also be avoided not only during neutralization but also in subsequent drying. Temperatures desirably do not exceed 45° C. during these steps and are preferably maintained in the range of 35° C. to 40° C.

Any proportion of borax may be used in the neutralization step, depending upon the desired ratio of boric acid to peroxyacid in the product, the amount of caustic soda or soda ash added being that then required to achieve the desired pH end point. Ordinarily, an amount of borax will be added to provide between one and two moles of boric acid per mol of peroxyacid in the product.

In order to achieve an adequate production of solids, the pH end point of such neutralization should be kept between about 2.0 and 6.0 and preferably between 2.5 and 5.0. The neutralization end point should be below 4.0 and preferably not above 3.5 in order to avoid excessive decomposition of the peroxyacid. The optimum end point pH is 2.5 to 3.0.

We claim:

1. A continuous method of producing peroxycarboxylic acid compositions from corresponding carboxylic acids having no substantial solubility in water comprising establishing in each of at least one reaction vessel comprising a reaction system a reaction mass consisting of a reaction phase having intimately interdispersed therethrough by continuous agitation an organic solvent not substantially miscible therewith and in which said carboxylic acid is not substantially soluble but in which said peroxycarboxylic acid has substantial solubility, said reaction phase consisting of said carboxylic acid, a concentrated strong acid in which said carboxylic acid is substantially soluble, hydrogen peroxide, and resulting reaction products, continuously introducing feed into the first vessel of said system while continuously withdrawing as effluent from the last vessel of said system a portion of said reaction mass contained therein and while continuously transferring from the next preceding vessel, if any, a portion of the reaction mass contained therein to the next succeeding vessel, if any, said feed being made up of hydrogen peroxide, said organic solvent and a solution of said carboxylic acid in said strong acid, and recovering product from said effluent in a cycle comprising first diluting the effluent with mother liquor recovered and recycled from prior effluent, which may be water-reduced, distilling the organic solvent from the diluted effluent, leaving an aqueous liquor containing crystals of the peroxycarboxylic acid previously dissolved in the organic solvent, reacting the acid of the aqueous liquor with borax to form a slurry of boric acid and sodium salt of the strong acid in an aqueous mother liquor, recycling to the step of dilution of the effluent at least the mother liquor portion of said slurry, which may be water-reduced, and separating as product a mixture of crystals of peroxycarboxylic acid, boric acid and said sodium salt from the aqueous liquid with which they are associated in said cycle at a point at which said crystals of all said substances are simultaneously present.

2. The method of claim 1 wherein the carboxylic acid is a carboxy alkane containing between 6 and 20 carbon atoms.

3. The method of claim 2 wherein the carboxy alkane is a dicarboxy alkane.

4. The method of claim 2 wherein the strong acid is sulfuric acid having a concentration corresponding to between a 10% molar excess of $H_2O$ and a 20% molar excess of $SO_3$ beyond the stoichiometric ratio of $H_2O$ and $SO_3$ in $H_2SO_4$.

5. The method of claim 1 or claim 4 wherein the reaction mass is maintained at a temperature between 25° C. and 100° C. and the boiling point of the organic solvent is at the reaction temperature of the reaction mass, the volume of said organic solvent in the reaction mass is at least four times the total volume of the remaining components and the concentration of the hydrogen peroxide used as part of the feed is 30% by weight.

6. The method of claim 5 wherein the effective residence time of the reaction mass in the system is between ½ hour and 2 hours.

7. A continuous method of producing diperoxydodecanedioic acid compositions from dodecanedioic acid comprising continuously introducing a feed, made up of aqueous hydrogen peroxide, methylene chloride as organic solvent and a solution of dodecanedioic acid in concentrated sulfuric acid, into the first vessel of a system made up of at least one stationary vessel equipped with a stirrer and a reflux condenser, said vessels being connected serially when more than one is present, each of said at least one vessel containing a reaction mass having the same components as the said feed together with resulting reaction products, the methylene chloride in each said reaction mass being continuously maintained in intimate interdispersion with the other components by action of the stirrer, continuously withdrawing as effluent from the last vessel of said system a portion of the reaction mass contained therein, continuously transferring from the next preceding vessel, if any, a portion of the reaction mass contained therein to the next succeeding vessel, if any, and recovering peroxydodecanedioic acid from said withdrawn portion, the temperature of each said reaction mass being maintained at about 40° C. with reflux of vaporized methylene chloride, the concentration of said aqueous hydrogen peroxide being at least 40% by weight, the concentration of said sulfuric acid corresponding to between 4% molar excess of $H_2O$ and 4% molar excess of $SO_3$ beyond the stoichiometric ratio of $H_2O$ to $SO_3$ in $H_2SO_4$, the molar ratio of hydrogen peroxide to dodecanedioic acid in said feed being between 3:1 and 3.5:1, the molar ratio of sulfuric acid to dodecanedioic acid in said feed being between 3:1 and 3.5:1, the volume ratio of said methylene chloride to the other components in said reaction mass, and in said feed, being about 5:1, the volume rate of introduction of said feed into the system and withdrawal of reaction mass portion from said system being such in comparison to the total volume of reaction mass in the system that the effective residence time of the reaction mass in the system is about one hour, and recovering product from said effluent in a cycle comprising first diluting the effluent with mother liquor recovered and recycled from prior effluent, which may be water-reduced, distilling the organic solvent from the diluted effluent, leaving an aqueous liquor containing crystals of the peroxycarboxylic acid previously dissolved in the organic solvent, reacting the acid of the aqueous liquor with borax to form a slurry of boric acid and sodium salt of the sulfuric acid in an aqueous mother liquor, recycling to the step of dilution of the effluent at least the mother liquor portion of said slurry, which may be water-reduced, and separating as product a mixture of crystals of peroxycarboxylic acid, boric acid and said sodium salt from the aqueous liquid with which they are associated in said cycle at a point at which crystals of all said substances are simultaneously present.

8. The method of claim 1 or claim 7 wherein the mixture of crystals of peroxycarboxylic acid, boric acid and sodium salt is separated from the mother liquor portion of said slurry before said mother liquor portion is recycled to the step of dilution of the effluent.

9. The method of claim 1 or claim 7 wherein the mother liquor from prior effluent is recycled to the step of dilution of the effluent while it contains the crystals of boric acid and sodium salt produced in the treatment of the prior effluent, whereby the aqueous liquor remaining after the step of distillation of the organic solvent contains a mixture of crystals of peroxycarboxylic acid, boric acid and sodium salt, and said mixture of crystals is separated as product from the said aqueous liquor before said aqueous liquor is reacted with said borax.

* * * * *